United States Patent [19]
Rich et al.

[11] Patent Number: 4,918,197
[45] Date of Patent: * Apr. 17, 1990

[54] SILYLATION METHOD

[75] Inventors: Jonathan D. Rich, Rexford; Terry E. Krafft, Schenectady; Philip J. McDermott, Clifton Park, all of N.Y.

[73] Assignee: General Electric Company, Schenectady, N.Y.

[*] Notice: The portion of the term of this patent subsequent to Aug. 5, 2003 has been disclaimed.

[21] Appl. No.: 232,242

[22] Filed: Aug. 15, 1988

Related U.S. Application Data

[63] Continuation-in-part of Ser. No. 33,567, Apr. 3, 1987, abandoned.

[51] Int. Cl.$^4$ .............................. C07F 7/08; C07F 7/10; C07F 7/18
[52] U.S. Cl. .................................... 548/406; 548/473; 549/214; 556/426; 556/431; 556/437; 556/432; 556/435; 556/415; 556/416; 556/417; 556/422; 556/436; 556/443; 556/444; 556/450; 556/452; 556/453; 556/456; 556/460; 556/468
[58] Field of Search ................ 548/406, 473; 549/214; 556/426, 431, 427, 432, 435, 415, 416, 417, 422, 436, 443, 444, 450, 452, 453, 456, 460, 468

[56] References Cited

U.S. PATENT DOCUMENTS

| | | | |
|---|---|---|---|
| 3,487,112 | 6/1967 | Paulik et al. | 260/604 |
| 3,726,809 | 4/1973 | Allum et al. | 252/431 P |
| 3,832,404 | 8/1974 | Allum et al. | 260/604 HF |
| 4,083,803 | 4/1978 | Oswald et al. | 252/430 |
| 4,410,669 | 10/1983 | Panster et al. | 525/474 |
| 4,709,054 | 11/1987 | Rich | 556/435 X |

OTHER PUBLICATIONS

Alumm, K. G. et al., "Supported Transition Metal Complexes, V, Liquid Phase Catalytic Hydrogenation of Hexene-1, Cyclohexene & Isoprene Under Continuous Flow Conditions", Journal of Catalysis 43, (1976), pp. 331-338.
Grubbs, R. H., "Hybrid-Phase Catalysts", Chemtech, (Aug. 1977), pp. 512-518.
Allum, K. G. et al., "Supported Transition Metal Complexes, II, Silica as the Support", Journal of Organometallic Chemistry 87, (1975), pp. 203-216.
Capka, M. & Hetflejs, J., "Hydrosilylation Catalysed by Transition Metal Complexes Coordinately Bound to Inorganic Supports", Collection Czechoslov. Chem. Commun. 39, (1974), pp. 154-166.
Pittman et al., Journal of the American Chemical Society; "Catalytic Reactions Using Polymer-Bound vs. Homogeneous Complexes of Nickel, Rhodium and Ruthenium", (1975), pp. 1742-1748.
Bailey et al., Chemical Reviews, vol. 81, No. 2, (1981), "Immobilized Transition-Metal Carbonyls and Related Catalysts"; pp. 109-148.

Primary Examiner—Paul F. Shaver
Attorney, Agent, or Firm—William A. Teoli; James C. Davis, Jr.; William H. Pittman

[57] ABSTRACT

A method is provided for silylating aromatic acylhalide by effecting reaction between an aromatic acylhalide and halogenated polysilane in the presence of an effective amount of a supported transition metal catalyst, such as a transition metal catalyst supported by an organic or inorganic substrate.

21 Claims, No Drawings

SILYLATION METHOD

CROSS-REFERENCE TO RELATED APPLICATIONS

This application is a continuation-in-part of copending application Ser. No. 033,567, filed Apr. 3, 1987, abandoned and incorporated herein by reference.

BACKGROUND OF THE INVENTION

In U.S. Pat. No. 4,709,054, there is described a method for silylating aromatic acylhalide with halogenated polysilane in the presence of an effective amount of a transition metal catalyst. As shown by Yamamoto et al., Tetrahedron Letters, 1653 (1980) activated aromatic acylhalide, such as para-nitrobenzoylchloride, can be converted to the corresponding aromatic silane with a loss of carbon monoxide as a result of a decarbonylation reaction utilizing hexamethyldisilane as the silylating reactant. It was found, however, that the silylation of the aromatic nucleus using hexamethyl disilane, resulted in only a minor amount of the desired aromatic silane, such as a paranitrophenyltrimethylsilane, while the major product was the corresponding aromatic silylketone.

In U.S. Pat. No. 4,709,054 (Rich), assigned to the same assignee as the present invention and incorporated herein by reference, there is taught that if halogenated polysilane of the formula,

(1)

is reacted with aromatic acylhalide of the formula,

(2)

in the presence of an effective amount of a transition metal catalyst, a wide variety of aromatic silylation reaction products can be obtained at high yields resulting in the production of nuclear-bound carbon-silicon bonds, where X is a halogen radical, R is selected from X, hydrogen, $C_{(1-13)}$ monovalent hydrocarbon radicals, substituted $C_{(1-13)}$ monovalent hydrocarbon radicals, and divalent —O—, —S— radicals and mixtures thereof which can form ≡SiOSi≡ and ≡SiSSi≡ connecting groups, $R^1$ is a $C_{(6-20)}$ monovalent or polyvalent aromatic organic radical, n is an integer equal to 1 to 50 inclusive, and m is an integer equal to 1 to 4 inclusive.

Although the method of U.S. Pat. No. 4,709,054 provides for the production of organic salines and silarylenes at high yields, it has been found difficult to recycle, regenerate or salvage transition metal catalyst values from the reaction mixture.

In copending application, Ser. No. 033,567, there is discussed the use of a transition metal complex supported by an inorganic substrate having chemically combined groups of the formula,

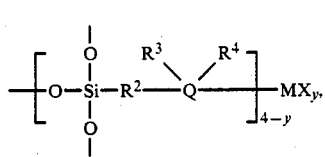
(3)

where $R^2$ is a divalent $C_{(2-14)}$ organic radical, Q is a nitrogen or phosphorous radical, $R^3$ and $R^4$ are monovalent $C_{(1-14)}$ alkyl or aryl radicals, M is a transition metal selected from palladium, platinum, rhodium or nickel, X is previously defined, y is an integer equal to 1 to 3 inclusive and preferably 2.

The present invention is based on the discovery that a wide variety of silylated aromatic reaction products having one or more nuclear-bound silicon atoms joined to an aromatic nucleus by carbon-silicon bonds also can be made by effecting reaction between halogenated polysilane of formula (1) and aromatic acylhalide of formula (2) in the presence of an effective amount of a transition metal complex supported by an organic substrate. Support to an organic substrate can be achieved through chemically combined groups of the formula

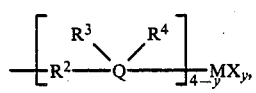
(4)

where $R^2$, $R^3$, and $R^4$, M, X and y are as previously defined. Surprisingly, supported transition metal complexes of the present invention having chemically combined groups of formulas (3) or (4) have been found to be recyclable at the termination of the reaction. In addition, supported complexes having chemically combined groups of formula (3) also can be regenerated at the end of the reaction.

STATEMENT OF THE INVENTION

There is provided by the present invention, a method for making silylated aromatic organic materials having at least one nuclear-bound silicon atom attached to an aromatic organic group by a carbon-silicon linkage comprising, (A) effecting reaction between a halogenated polysilane of formula (1) and aromatic acylhalide of formula (2) in the presence of an effective amount of a supported transition metal complex having chemically combined groups of formula (3) or (4), and (B) recovering silylated aromatic organic material from the mixture of (A).

Some of the supported transition metal complexes of formula (3) which can be used in the practice of the present invention and which are incorporated herein by reference are shown by A. G. Allum et al., "Supported Transition Metal Complexes II Silica as the Support", Journal of Organometallic Chemistry 87 (1975), pp. 203–216, and M. Capka et al., "Hydrosilylation Catalyzed By Transition Metal Complexes Coordinately Bound to Inorganic Supports", Collection Czechoslov. Chem. Commun., Vol. 39, pp. 154 (1974). Additional supported transition metal catalysts which can be used are shown by U.S. Pat. No. 4,083,803, Oswald et al., U.S. No. 3,487,112, U.S. Pat. No. 3,726,809, and U.S. No. 3,832,404 also incorporated herein by reference. There are included for example, in addition to silica, alumina and zeolites. The silica substrate can be in the form of silica extrudate.

A preferred substrate to which groups of formula (4) can be attached is polystyrene. Catalysts of this type have been previously described. For example, see D. C. Bailey et al., "Immobilized Transition-Metal Carbonyls and Related Catalysts", Chemical Reviews 81 (1981), pp. 110-121, C. U. Pittman et al., "Catalytic Reactions Using Polymer-Bound vs. Homogeneous Complexes of Nickel, Rhodium, and Ruthenium", J. Am. Chem. Soc. 97 (1975), pp. 1742-1748, J. D. Allen, U.S. Pat. No. 3,847,997 and S. V. McKinley et al., U.S. No. 3,708,462.

Among the halogenated polysilanes which are included within formula (1) there are, for example, chloropentamethyldisilane, 1,2-dichlorotetramethyldisilane, 1,1-dichlorotetramethyldisilane, 1,1,2-trimethyltrichlorodisilane, 1,1,2,2-tetrachlorodimethyldisilane, hexachlorodisilane, 1,2-dibromotetramethyldisilane, 1,2-difluorotetramethyldisilane, 1,1,2,2,4,4,5,5-octamethyl-1,2,4,5-tetrasilacyclohexasiloxane, 1-chlorononamethyl-tetrasil-3-oxane, 1,2-dichloro-1,2-diphenyldimethyldisilane, etc.

Some of the aromatic acyl halides which are included within formula (2) are, for example, monofunctional aromatic acyl halide such as benzoyl chloride, trimellitic anhydride acid chloride, chlorobenzoyl chloride, anisoyl chloride, nitrobenzoyl chloride, toluoyl chloride, cyanobenzoyl chloride, bromobenzoyl chloride, dimethylaminobenzoyl chloride, N-n-butyl trimellitic imide acid chloride, etc.

Polyfunctional aromatic polyacyl halides which are included within formula (2) are, for example, terephthaloyl chloride, phthaloyl chloride, isophthaloyl chloride, etc.

There are included among organic silanes which can be made in accordance with the practice of the method of the present invention compounds such as phenyldimethylchlorosilane, phenylmethyldichlorosilane, chlorophenyldimethylchlorosilane, anisyldimethylchlorosilane, nitrophenyldimethylchlorosilane, tolyldimethylchlorosilane, cyanophenyldimethylchlorosilane, 4-dimethylchlorosilylphthalic anhydride, N-n-butyl-4-dimethylchlorosilyl phthalimide, bromophenyldimethylchlorosilane, etc.

Radicals which are included within R of formula (1) are, for example, $C_{(1-8)}$ alkyl radicals, for example methyl, ethyl, propyl, butyl, pentyl, etc., chlorobutyl, trifluoropropyl, cyanopropyl; aryl radicals, for example phenyl xylyl, tolyl, naphthyl, halogenated aryl radicals such as chlorophenyl, dichlorophenyl, trichlorophenyl, fluorophenyl, difluorophenyl, bromophenyl; nitro and polynitro aromatic radicals as well as aryl ether radicals, for example, anisole, ethoxyphenyl, propoxyphenyl, diphenylether, cyanophenyl, etc.

Some of the monovalent aromatic radicals and substituted aromatic radicals which can be included within $R^1$ of formula (2) are, for example, phenyl, xylyl, tolyl, naphthyl; halogenated aromatic radicals such as chlorophenyl, dichlorophenyl, trichlorophenyl, etc., fluorophenyl, difluorophenyl, etc., bromophenyl, dibromophenyl, etc.; nitro and polynitro aromatic radicals as well as aryl ether radicals for example, anisoyl, ethoxyphenyl, propoxyphenyl, diphenylether. Additional substituted aromatic radicals which can be included within $R^1$ are for example, cyanophenyl, polycyanophenol, as well as phthalimido radicals.

Radicals included within $R^2$ of formulas (3) and (4) are ethylene, propylene, butylene, octylene, tetradecylene, phenylene, phenylmethylene, phenylethylene and phenylpropylene; $R^3$ and $R^4$ are selected from methyl, ethyl, propyl, butyl, and isomers thereof, cyclopentyl, cyclohexyl, phenyl, tolyl, xylyl, mesityl and anisyl; and X is selected from Cl, Br, I.

Examples of the inorganic substrate supported catalyst of formula (3) are,

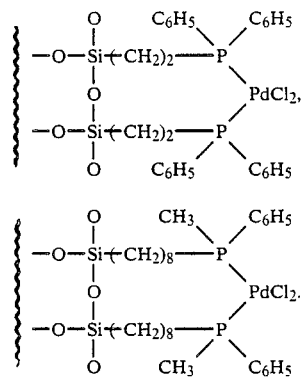

A preferred example of the organic supported substrate of groups included within formula (4) is

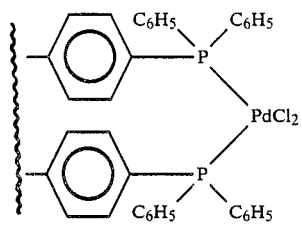

There are also included among the aromatic silylation reaction products, silarylene halides, such as 1,4-(bis-chlorodimethylsilyl)benzene. The synthesis of such silphenylene compounds can be made from terephthaloyl chloride and 1,2-dichlorotetramethyldisilane.

An effective amount of the inorganic, or organic substrate supported catalyst, such as the silica supported transition metal catalyst, is an amount of supported transition metal catalyst which is sufficient to provide fro 0.005% by weight to 20% by weight of transition metal based on the weight of aromatic acyl halide.

In the practice of the present invention, reaction is initiated between the halogenated polysilane of formula (1) and the aromatic acylhalide of formula (2) in the presence of an effective amount of the supported transition metal catalyst. Reaction can be carried out under a variety of conditions. For example, the reactants can be heated to the desired temperature in the absence of solvent, while being stirred under an inert atmosphere or in the presence of a nonreactive solvent with a boiling point greater than about 100° C. to 300° C. Nonreactive solvents which can be used are, for example, o-xylene, anisole, mesitylene, or nonhalogenated aromatic or aliphatic solvents.

Depending upon the value of m in formula (2) for the aromatic acylhalide, and whether the halogenated polysilane is a monofunctional or polyfunctional halopolysilane, molar proportions of the halogenated polysilane and the aromatic acylhalide can vary widely. There should be used sufficient halogenated polysilane to provide at least 2 gram atoms of silicon of the halogenated polysilane, per mole of the aromatic acylhalide.

Temperatures which can be utilized in effecting reaction between the halogenated polysilane and the aromatic acylhalide are, for example, 110° C. and preferably 135°-145° C. depending upon the nature of the reactants and conditions utilized, such as with or without organic solvent, as previously discussed.

Organic silanes made in accordance with the practice of the present invention can be hydrolyzed to a variety of valuable intermediates, such as silarylenesilane diols, bis(siloxaneanhydrides), bis(siloxaneimides), etc.

In order that those skilled in the art will be better able to practice the present invention, the following examples are given by way of illustration and not by way of limitation. All parts are by weight.

EXAMPLE 1

There was added 17.67 grams (0.10 moles) of palladium dichloride to a mixture of 75 grams (0.20 moles) of diphenylphosphinoethyltriethoxysilane dissolved in 200 ml of dry dichloroethane. The diphenylphosphinoethyltriethoxysilane was prepared in accordance with the method of A. G. Allum et al., Journal Organomet. Chem. 87, 203 (1975). The mixture of palladium dichloride and the triphenylphosphinoethyltriethoxysilane was heated to reflux until all of the suspended palladium dichloride was consumed. The resulting orange solution was alluted with 100 ml hexane. Upon cooling there was formed 89.9 grams (97%) of bis(diphenylphosphinoethyltriethoxysilyl)palladium dichloride as yellow crystals.

There was added 585 grams of ⅛ in. diameter silica extrudates to 60.7 grams of bis(diphenylphosphinoethyltriethoxysilyl)palladium dichloride dissolved in 500 ml of methylene chloride. The color of the resulting solution changed and the extrudates were yellow orange. The catalyst was filtered and washed with methylene chloride and air-dried at 125° C. for two hours. Extrudates were then added to 700 ml of 5% aqueous HCl and allowed to stand for 12 hours followed by filtration, washing with water and subsequently acetone, ether and pentane. The resulting catalyst was then air-dried at 125° C. for eight hours. The catalyst was then immersed in an excess of hexamethyldisilazane for two hours at room temperature, followed by filtration, washing with methylene chloride and pentane and drying under vacuum at 80° C. for 15 hours. There was obtained a silica supported palladium silylation catalyst having a plurality of chemically combined groups of the formula,

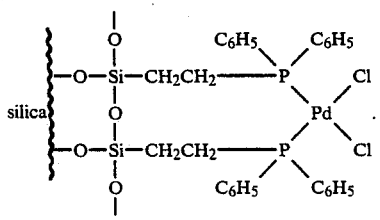

Chemical analysis showed that the catalyst contained 2.02% by weight of palladium.

There was heated neat to 145° C., a mixture of 562 grams (2.67 moles) trimellitic anhydride acid chloride, 700 grams (2.67 moles) of 1,2-dichlorotetramethyldisilane and 40 grams (0.3 mole %) of the above silylation catalyst having 2.02% by weight of palladium. Rapid outgassing of carbon monoxide occurred from the catalyst surface and dimethyldichlorosilane formed during reaction was continuously removed by distillation. After heating the mixture for 12 hours at 145° C., gas chromatography indicated complete reaction of the trimellitic anhydride acid chloride. The resulting mixture was then decanted. Vacuum distillation resulted in the production of 169 grams (73% yield) of 4-chlorodimethylsilylphthalic anhydride as a clear liquid, b.P. 141° C./0.1 torr.

EXAMPLE 2

The procedure of Example 1 was repeated for making the silica supported palladium catalyst except that there was used 89.9 grams (0.16 mole) of bis(diphenylphosphinoethyl)triethoxysilane and 1,064 grams of 200-300 mesh silica. Based on method of preparation and chemical analysis, there was obtained a silica supported palladium catalyst having about 1% by weight of palladium.

A reaction mixture containing 203 grams (1.0 mole) of terephthaloylchloride and 187 grams (1.0 mole) of 1,2-dichlorotetramethyldisilane was stirred and heated neat to 245° C. until a homogeneous mixture was obtained. There was added to the mixture, 32 grams of the silica supported 1% palladium catalyst. Rapid evolution of carbon monoxide gas occurred and dimethyldichlorosilane was removed continuously as it formed. After 12 hours at 145° C. NMR analysis showed complete reaction of the terephthaloylchloride. The reaction mixture was cooled to room temperature and filtered under nitrogen to remove the catalyst. Distillation of the mixture provided 174 grams (75%) yield of 4-chlorodimethylsilylbenzoylchloride as a clear liquid, boiling point 97° C./0.1 torr.

EXAMPLE 3

The procedure of Example 2 was repeated utilizing 10 grams (4.93×10⁻²  moles) of terephthaloylchloride, 9.2 grams (4.93×10⁻² moles) of 1,2-dichloroetetramethyldisilane and 3 grams of the 1% palladium (II0) on silica from Example 2. The mixture was heated to 145° C. neat. There was also utilized in the mixture, an unreactive GC internal standard, tetradecane (3.16 grams, 1.63×10⁻² moles). After three hours, the reaction was stopped and the progress of the reaction was monitored by gas chromatography. The same procedure was repeated except that in place of the 3 grams of reused silica supported 1% palladium prepared in Example 2, there was used 3 grams of a 1% commercially available palladium on carbon, Johnson-Mathey Corporation TS2276. An additional reaction was also run employing 3 grams of a commercially-available silica supported 1% palladium catalyst from Engelhardt Company. It was determined that the latter commercially available silica supported palladium catalyst had the palladium absorbed onto the surface of the silica instead of being chemically combined, as shown in Examples 1 and 2.

The various mixtures was heated continuously for 3 hours under neat conditions and the progress of the respective reactions was monitored by gas chromatography. The catalysts were then filtered, washed with methylene chloride, dried under nitrogen and reintroduced into fresh aliquots of the respective reaction mixtures. It was found that the reaction mixture containing the commercially available silica supported palladium catalyst which was absorbed onto the surface of the silica, could not be satisfactorily monitored, as little or no reaction had occurred. However, the results of five runs were monitored, as shown in the drawing, comparing the reaction mixture catalyzed by the silica supported palladium catalyst having palladium chemically combined to silica through connecting groups of formula (4), "Rich" and the reaction mixture containing the "Commercial" palladium catalyst used carbon as a support. After three runs, the respective catalysts were removed from the mixtures, slurried in carbon tetrachloride, and gaseous chlorine was introduced. The Rich catalyst of the present invention turned yellow-orange in color and the rate of color change could be increased by mildly heating the carbon tetrachloride following filtration and washing with methylenechloride. After the catalysts were dry, they were reintroduced in fresh aliquots of starting materials. It was found that the "reactivated" catalyst of the present invention "Rich" showed 85% of its initial activity from the first run, while no change was noted in the commercially available catalyst.

EXAMPLE 4

After several runs, the silica supported catalyst of Example 1, a batch of 2% palladium on ⅛" silica extrudates, had been completely reduced to palladium black and was no longer active in the silylation process. The spent silica supported palladium catalyst was then slurred in a 5% aqueous solution of copper chloride for 10 minutes and oxygen was then bubbled through the mixture. An exothermic reaction occurred and the silica supported palladium catalyst turned from black to yellow-orange in color. The mixture was then filtered and the silica supported palladium catalyst was then analyzed. Elemental analysis showed that the spent catalyst had 1.3% palladium while the original was 2.02% palladium. After the spent catalyst was reoxidized, the reactivated catalyst contained 0.7% palladium and 1% copper.

A reaction mixture containing 4.93×10$^{-2}$ moles of trimellitic anhydride acid chloride and 4.93×10$^{-3}$ moles of 1,2-dichlorotetramethyldisilane was heated to 145° in the presence of 3 grams of the above-described silica supported reactivated catalyst. After 3 hours at 145° C., 998 chromatography indicated complete reaction of the trimellitic anhydride acid chloride. The resulting mixture was then decanted and vacuum distilled to provide 7.23 grams or a 61% yield of 4-chloromethylsilylphthalic anhydride.

EXAMPLE 5

The procedure of Example 2 was repeated for making the 1% by weight of palladium catalyst.

A reaction mixture containing 3 gram (2.13×10$^{-2}$ mole) of benzoyl chloride and 4.85 grams (2.13 mole) or sym-tetrachlorodimethyl disilane was stirred and heated to 130°–135° C. neat until a homogeneous mixture was formed. There was added to the mixture 2.2 g of 1% palladium on 200-300 mesh silica. Rapid evolution of carbon monoxide occurred and trichloromethylsilane was removed continuously as it formed. After 15 hours at 130° C., NMR analysis showed complete reaction of benzoyl chloride.

The above reaction was repeated with other substrates, as shown by the following equation and Table, where Ar is phenyl, or substituted phenyl:

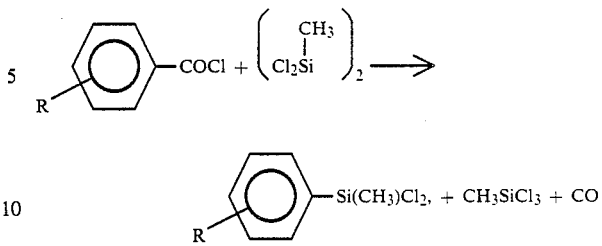

TABLE

| Substrate where R = | Mole % ArSiCH$_3$Cl$_2$ | Mole % ArCl |
|---|---|---|
| H | 90 | 10 |
| P—Cl | 89 | 11 |
| P—COCl | 88 | 12 |
| 3,4 phthalimide N—CH$_3$ | 36 | 7 |
| 3,4 phthalic anhydride | 95 | 5 |

The above results show that the silica supported catalyst of the present invention having chemically combined groups of formula (4), has superior selectivity when used to make polyfunctional aryl silanes from aryl substrates substituted with a variety of activating groups employing polysilanes having silicon atoms with at least two halogen radicals per silicon.

In contrast, a similar silylation reaction was conducted with the same substrates using the 1% commercially available palladium on carbon catalyst of Example 3. It was found that a wide variation resulted in selectivity in accordance with the substituent R on the phenyl ring. For example, when R was hydrogen, only a trace of the desired phenyl silane was obtained while a 78% yield was obtained with chloroacylphthalicanhydride. A 67% yield was obtained with terephthaloyl chloride.

EXAMPLE 6

Bisbenzonitrile palladium dichloride (19.2 mg, 5.0×10$^{-5}$ moles) and beads of polymer bound triphenylphosphine (194 mg, 1.2×10$^{-4}$ moles of phosphorous) were stirred together with 10 ml of dichloromethane. The polymer beads consisted of polystyrene which was 2% crosslinked with divinylbenzene and substituted with triphenylphosphine. The mixture was stirred for 15 minutes at room temperature, during which time the orange color of the palladium complex was transferred from solution to the polymer beads. The orange beads were isolated by filtration, washed with CH$_2$Cl$_2$, and dried under vacuum.

There was heated neat to 120° C., a mixture of 10.54 grams (0.05 moles) trimellitic anhydride acid chloride and all of the above silylation catalyst (0.1 mole % Pd). Addition of 9.36 grams (0.05 moles) 1,2-dichlorotetramethyldisilane over a 3-hour period resulted in outgassing of carbon monoxide from the catalyst surface and formation of dimethyldichlorosilane which was continuously removed from the reaction by distillation. After heating for 42 hours at 120° C., the reaction was cooled and the catalyst removed by filtration. Vacuum distillation of the reaction mixture yielded 9.73 grams (80% yield) of 4-chlorodimethylsilylphthalic anhydride.

EXAMPLE 7

The procedure of Example 6 was repeated using 10.54 grams (0.05 moles) trimellitic anhydride acid chloride, 9.36 grams (0.05 moles) 1,2-dichlorotetramethyldisilane and the silylation catalyst recovered from Example 6. After heating the reaction for 21 hours at 120° C., the catalyst was removed and the reaction mixture vacuum distilled to yield 10.24 grams (85% yield) of 4-chlorodimethylsilylphthalic anhydride.

EXAMPLE 8

The procedure of Example 6 for making 4-chlorodimethylsilylphthalic anhydride was repeated using the silylation catalyst recovered from Examples 6 and 7. After heating for 24 hours, vacuum distillation yielded 10.76 grams (88% yield) of the desired product.

EXAMPLE 9

There was heated neat to 120° C., a mixture of 10.46 grams (0.05 moles) terephthaloylchloride and the silylation catalyst recovered from Examples 6, 7 and 8. Addition of 10.30 grams (0.055 moles) 1,2-dichlorotetramethyldisilane over a 1.5 hour period resulted in carbon monoxide evolution and formation of dimethyldichlorosilane. After heating for 40 hours at 120° C., gas chromatography showed that the starting material had completely reacted. Vacuum distillation yielded 10.67 grams (91% yield) of 4-chlorodimethylsilylbenzoylchloride.

Although the above examples are directed to only a few of the very many variables which can be utilized in the practice of the method of the present invention, it should be understood that the present invention is directed to a much broader variety of inorganic and organic substrate supported transition metal catalysts, halogenated polysilane and aromatic acylhalide shown in the description preceeding these examples.

What is claimed and sought to be protected by Letters Patent of the United States is as follows:

1. A method for making silylated aromatic organic material having at least one nuclear-bound silicon atom attached to an aromatic group by a carbon-silicon linkage comprising, (A) effecting reaction between a halogenated polysilane of the formula,

and aromatic acylhalide of the formula,

in the presence of an effective amount of a supported transition metal complex having chemically combined groups selected from the class consisting of,

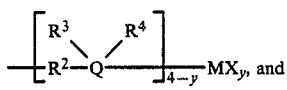

and

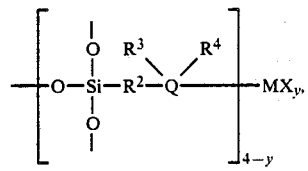

and
    (B) recovering silylated aromatic organic material from the mixture of (A), where X is halogen, M is a transition metal selected from palladium, platinum, or nickel, Q is a nitrogen or phosphorous radical, y is an integer having a value of from 1 to 3 inclusive, R is selected from X, hydrogen, $C_{(1-13)}$ monovalent hydrocarbon radicals, substituted $C_{(1-13)}$ monovalent hydrocarbon radicals, and divalent —O—, —S— radicals and mixtures thereof which can form $\equiv$SiOSi$\equiv$ and $\equiv$SiSSi$\equiv$ connecting groups, $R^1$ is a $C_{(6-20)}$ monovalent or polyvalent aromatic organic radical, $R^2$ is a divalent $C_{(2-14)}$ alkyl or aryl radical and $R^3$ and $R^4$ are monovalent $C_{(1-14)}$ alkyl or aryl radicals.

2. A method in accordance with claim 1, where the halogenated polysilane is 1,1,2,2-tetrachlorodimethyldisilane.

3. A method in accordance with claim 1, where the aromatic acylhalide is trimellitic acid chloride.

4. A method in accordance with claim 1, where the aromatic acylhalide is terepthaloylchloride.

5. A method in accordance with claim 1, where the aromatic acylhalide is isophthaloyl chloride.

6. A method in accordance with claim 1, where the halogenated polysilane is 1,2-dichlorotetramethyldisilane.

7. A method in accordance with claim 1, conducted in a continuous manner.

8. A method in accordance with claim 1, where the silyated aromatic organic material is organic silane.

9. A method in accordance with claim 1, where the silyated aromatic organic material is a silarylene.

10. A method in accordance with claim 8, where the organic silane is 4-chlorodimethylsilylphthalic anhydride.

11. A method in accordance with claim 8, where the organic silane is 4-chlorodimethylsilylbenzoyl chloride.

12. A method in accordance with claim 8, where the organic silane is N-butyl-4-chlorodimethylsilylphthalimide.

13. A method in accordance with claim 9, where the silarylene is 1,4-dichlorosilylphenylene.

14. A method in accordance with claim 1, where the aromatic acylhalide is 3-nitrobenzoyl chloride.

15. A method in accordance with claim 1, where the aromatic acylhalide is 4-nitrobenzoyl chloride.

16. A method in accordance with claim 1, where the aromatic acylhalide is benzoyl chloride.

17. A method in accordance with claim 1, where the supported catalyst has chemically combined groups of the formula

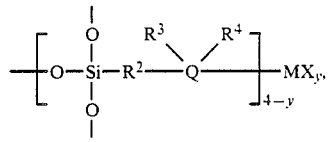

which are chemically reactivated with $Cl_2$ or $Cu^{II}Cl_2/O_2$.

18. A method in accordance with claim 1, where the supporting substrate is silica.

19. A method in accordance with claim 1, where the supporting substrate is alumina.

20. A method in accordance with claim 1, where the supporting substrate is organic polymer.

21. A method in accordance with claim 1, where the supporting substrate is polystyrene.

* * * * *